United States Patent [19]
Cushieri et al.

[11] Patent Number: 5,352,206
[45] Date of Patent: Oct. 4, 1994

[54] TROCAR SYSTEM HAVING PENETRATION INDICATOR

[75] Inventors: Alfred Cushieri, Hepburn Gardens, Scotland; Terry Buelna, Long Beach, Calif.

[73] Assignee: Laparomed Corporation, Irvine, Calif.

[21] Appl. No.: 40,551

[22] Filed: Mar. 31, 1993

[51] Int. Cl.⁵ .............................................. A61M 5/178
[52] U.S. Cl. .................................. 604/164; 604/158; 604/264; 606/185
[58] Field of Search ............... 604/164, 161, 165, 168, 604/117, 118, 264; 606/185

[56] References Cited

U.S. PATENT DOCUMENTS

| | | | |
|---|---|---|---|
| 2,646,042 | 7/1953 | Hu | 604/118 |
| 2,976,865 | 3/1961 | Shipley | 604/118 |
| 3,982,533 | 9/1976 | Wiest . | |
| 4,254,762 | 3/1981 | Yoon | 128/754 |
| 4,331,138 | 5/1982 | Jessen | 128/207.29 |
| 4,404,924 | 9/1983 | Goldberg et al. | 116/270 |
| 4,535,773 | 8/1985 | Yoon | 604/118 |
| 4,623,335 | 11/1986 | Jackson | 604/118 |
| 4,710,172 | 12/1987 | Jacklich et al. | 604/118 |
| 4,801,293 | 1/1989 | Jackson | 604/51 |
| 4,943,280 | 7/1990 | Lander | 604/169 |
| 4,944,724 | 7/1990 | Goldberg et al. | 604/118 |
| 5,053,016 | 10/1991 | Lander | 604/169 |
| 5,122,122 | 6/1992 | Allgood | 604/174 |
| 5,127,909 | 7/1992 | Schichman | 604/165 |
| 5,152,744 | 10/1992 | Plyley et al. | 604/164 |
| 5,207,647 | 5/1993 | Phelps | 604/158 |

Primary Examiner—John G. Weiss
Attorney, Agent, or Firm—Townsend and Townsend Khourie and Crew

[57] ABSTRACT

A trocar system comprises an obturator and a trocar cannula. The obturator includes an elongate shaft having a tapered distal end and a proximal end. At least one port is provided near the distal tip of the tapered distal end and open to an axial lumen within the obturator. A mechanism for producing an audible signal in response to superatmospheric pressure at the port, typically a whistle structure, is provided near the proximal end of the trocar. In this way, when the trocar system is introduced to an insufflated region during laparoscopic surgery, an audible whistle will be provided to alert the treating surgeon.

13 Claims, 3 Drawing Sheets

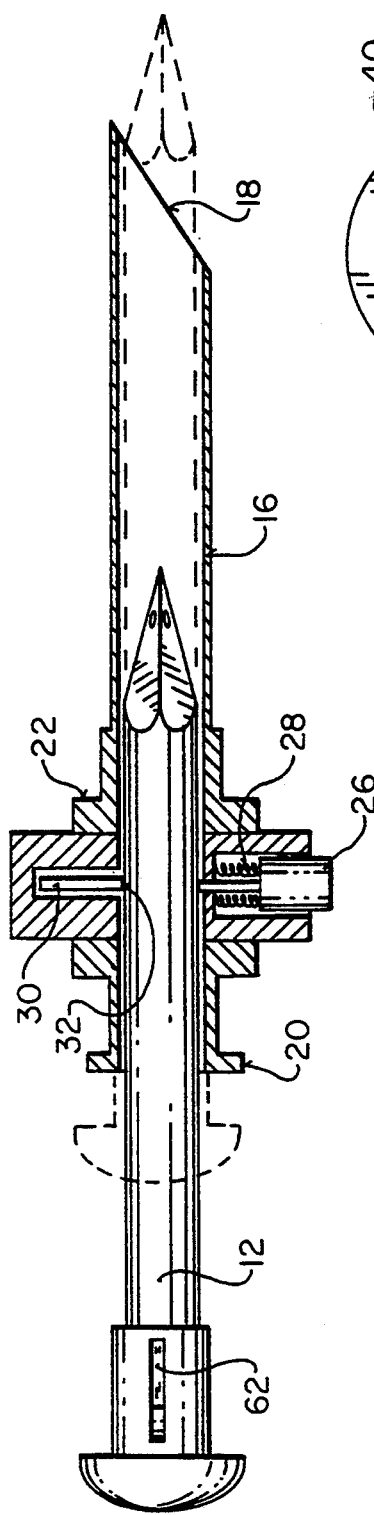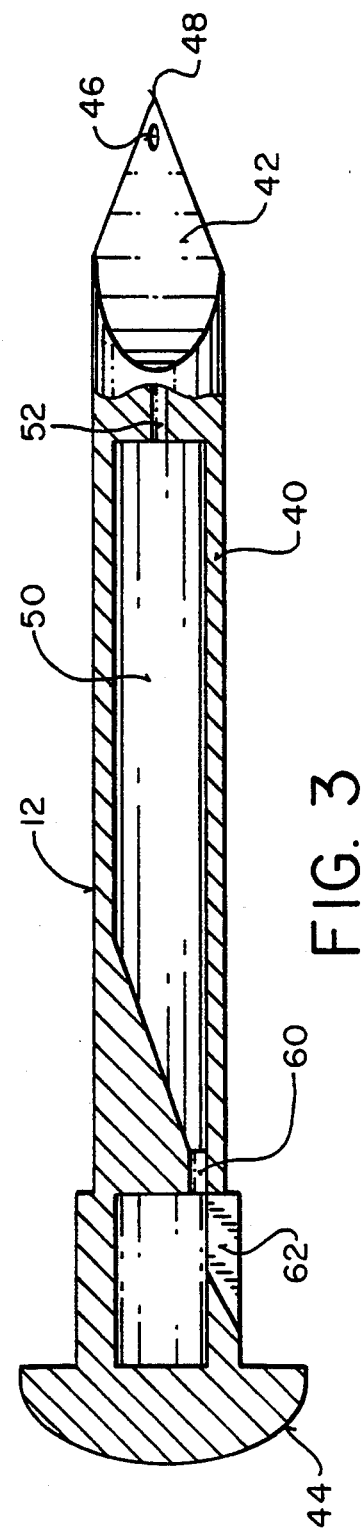

TROCAR SYSTEM HAVING PENETRATION INDICATOR

BACKGROUND OF THE INVENTION

1. Field of the Invention

The present invention relates generally to medical devices and more particularly to an improved trocar system having a mechanism for producing an audible signal when the trocar penetrates into an insufflated (pressurized) body cavity.

Least invasive surgical (LIS) techniques, such as laparoscopic, endoscopic, and arthroscopic surgery, are generally performed through small incisions using specialized instruments to perform desired surgical procedures. Usually, the instruments are introduced through a tube, such as a trocar cannula, while the physician observes manipulation of instruments through specialized imaging equipment, such as laparoscopes, endoscopes, arthroscopes, and the like. Such LIS techniques offer significant advantages over convention "open" surgical procedures. In particular, the LIS techniques are usually less traumatic, require a shorter recovery time, and are less costly than the corresponding conventional surgical technique.

Of particular interest to the present invention, laparoscopic surgery is generally performed within the abdominal cavity, with the abdominal wall raised by pressurization of the abdominal cavity (referred to as "insufflation" to create an open space for positioning of the laparoscope and manipulation of the surgical tools to perform the desired procedure. Insufflation is achieved by introducing an insufflation gas, typically carbon dioxide, through a Veress needle or other conduit which is introduced through the abdominal wall. One or more additional trocar cannulas are then introduced through the abdominal wall into the insufflated region between the abdominal wall and underlying organs created. Such trocar cannulas are typically introduced in combination with an obturator, which is a rigid shaft removably received within a central lumen of the trocar cannula and having a sharpened tip which extends out of the distal end of the cannula. In this way, the trocar cannula and obturator can together be penetrated through the abdominal wall relying on the sharpened distal end of the obturator. The obturator can then be removed, leaving the lumen of the trocar cannula available for access to the abdominal cavity.

While generally successful, the sharpened distal tip of the obturator presents a risk of injury to underlying body structures when the combined trocar cannula and obturator is introduced through the abdominal wall. In order to avoid such injury, it is important that the sharpened distal tip of the obturator be stopped or somehow protected immediately after the tip penetrates through posterior surface of the abdominal wall.

One such approach for protecting the tip relies on a spring-loaded shield mounted concentrically over the obturator. The shield is drawn proximally by contact with tissue as the obturator and trocar cannula are advanced through the abdominal wall. As soon as the obturator enters the abdominal cavity, however, the shield springs back over the sharpened tip of the obturator to protect underlying body organs from damage. Such an approach has been generally successful, but suffers from certain drawbacks. In particular, in some cases the shield may become jammed or may simply not respond quickly enough to cover the obturator before contact with body structures in the abdominal cavity occurs.

Even when responding as intended, the sharpened obturator tip is still able to penetrate beyond the tissue by a short distance, approximately 1 cm to 3 cm, before the shield redeploys over the entire length of the obturator. Thus, there remains a risk of injury during this length of unprotected travel. An alternative approach for protecting the obturator tip relies on a spring-loaded core within the obturator, where the core retracts as the obturator is advanced. Although an improvement over the external shield, the core can still become jammed.

For these reasons, it would be desirable to provide alternative apparatus and methods for protecting a patient during introduction of a trocar cannula and obturator system during surgical procedures, particularly laparoscopic procedures. It would be further desirable to provide protection which is responsive immediately as the sharpened distal tip of an obturator enters an insufflated abdominal cavity. Such apparatus and methods should be reliable, easy to implement, compatible with a wide variety of trocar cannula and obturator systems, and be relatively inexpensive to produce.

2. Description of the Background Art

Trocar cannula and obturator systems are known. See, e.g., U.S. Pat. Nos. 5,122,122; 5,127,909; 5,053,016; and 4,943,280. A drainage catheter which is introduced using a trocar and which includes a pressure-responsive silicone elastomer "signal dome" is disclosed in U.S. Pat. No. 4,944,724. Needles and syringes having pressure indicating devices are described in U.S. Pat. Nos. 4,801,293; 4,710,172; and 4,623,335. A Veress needle having a pressure gauge is disclosed in U.S. Pat. No. 3,982,533. Other patents relevant to the state-of-the-art include U.S. Pat. Nos. 4,404,924; 2,976,865; and 2,646,042. Karl Storz GmbH sells a trocar cannula and obturator system, where the obturator includes a pressure release vent which opens to a port immediately proximal to a sharpened distal tip.

SUMMARY OF THE INVENTION

According to the present invention, an obturator for use with a trocar cannula comprises an elongate shaft having a proximal end and a tapered distal end. A mechanism or means on the shaft is provided for producing an audible signal in response to superatmospheric pressure present at the distal tip of the shaft. Usually, the audible signal-producing mechanism will sense pressure through an axial lumen within the shaft via a port located very near the distal tip, typically within 2 mm of the tip, and preferably within 1 mm of the tip. In this way, the audible signal will be produced substantially immediately upon entrance of the obturator tip in an insufflated (superatmospheric) abdominal cavity. The surgeon will then be warned that the tapered distal end has entered the abdominal cavity and can take appropriate care.

In a preferred aspect of the present invention, the audible signal-producing mechanism will comprise a "whistle" structure, including a flow-restrictive orifice and a whistle aperture formed in the elongate shaft. The flow-restrictive orifice is positioned to produce a relatively high velocity gas stream past the whistle aperture so that a whistling sound will be produced as soon as the port at the distal tip of the shaft is exposed to the superatmospheric pressure of the insufflation gas.

The present invention further provides a trocar system comprising both the obturator, as described above, and a trocar cannula capable of receiving the obturator in a generally conventional manner.

The present invention still further provides a method for introducing a trocar cannula system into an insufflated region of a patient's abdomen. The method comprises advancing a combination trocar cannula and obturator through the abdominal wall, where a port at the distal tip of the obturator becomes exposed to the insufflated (superatmospheric) pressure as soon as its sharpened distal end enters the abdominal cavity. The obturator includes a mechanism for producing an audible signal, generally as described above, and the method further comprises stopping advancement of the trocar cannula and obturator after, typically after further advancement of the tube by 2 cm to 3 cm so that the trocar cannula is beyond the abdominal wall. In contrast to prior art methods and devices, the user will know that the obturator has broken through the wall and can take appropriate precautions, such as orienting the trocar generally parallel to the body, in order to lessen the risk of injury. After the trocar cannula has been fully penetrated, the obturator is then removed from the trocar cannula, leaving the cannula lumen available for introducing a laparoscope, surgical tool(s), or the like.

BRIEF DESCRIPTION OF THE DRAWINGS

FIG. 2 is a side, elevational view of the trocar system of FIG. 1, shown with the obturator partially advanced within the lumen of the trocar cannula (in full line) and with the obturator being fully advanced (in broken line).

FIG. 3 is a side, elevational view of the obturator of FIGS. 1 and 2, shown in partial section.

FIG. 3A is an end view of the obturator of FIG. 3, shown from the tapered distal end.

DESCRIPTION OF SPECIFIC EMBODIMENTS

Figure 1:
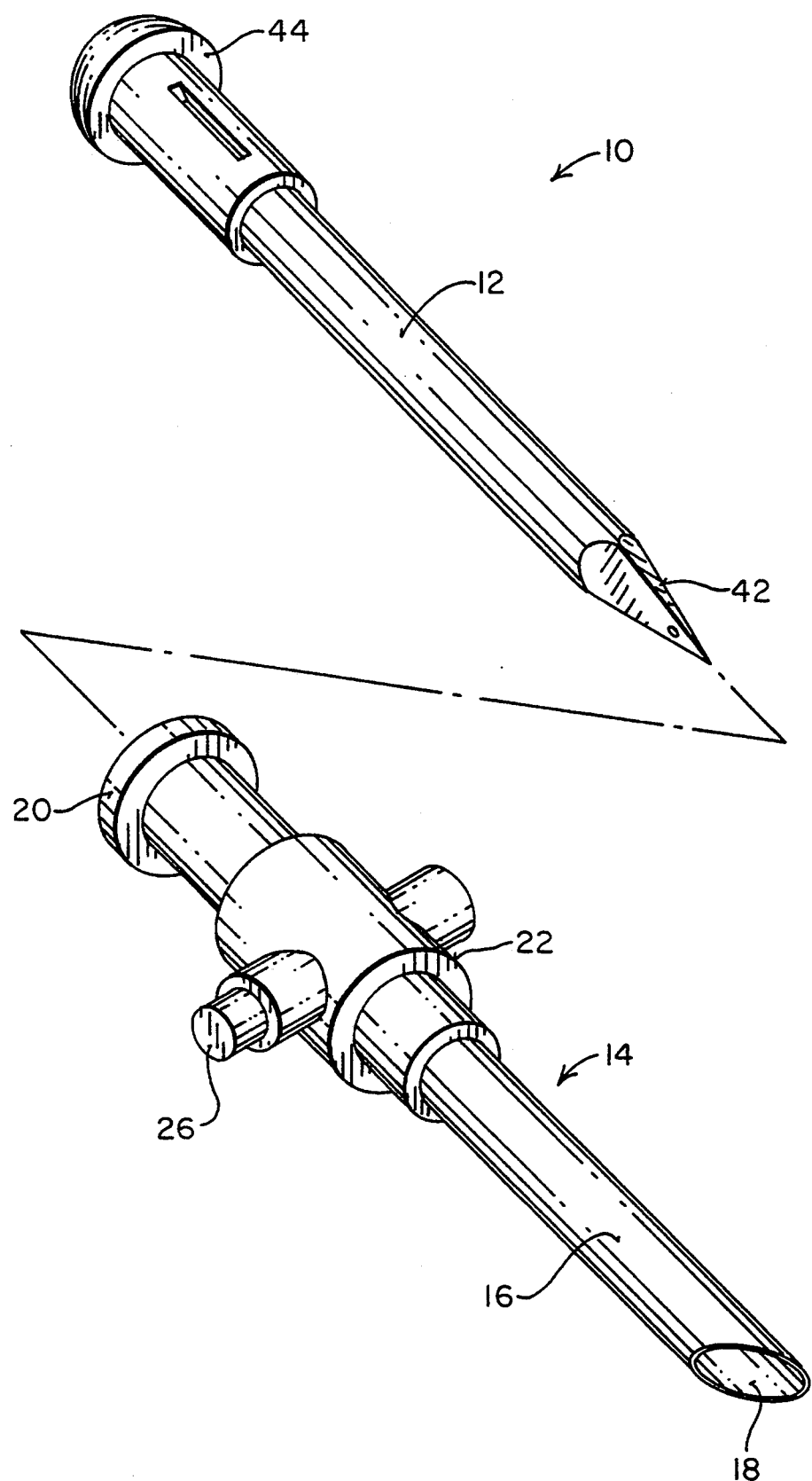
FIG. 1 is a perspective view of a trocar system comprising a trocar cannula and an obturator constructed in accordance with the principles of the present invention.

The obturators of the present invention will comprise an elongate shaft having a proximal end and a distal end. The shaft will typically be cylindrical, but could possess a variety of other cross-sectional geometries so long as they are compatible with introduction through an axial lumen of a trocar cannula, as described in greater detail hereinafter. The distal end of the obturator will be tapered to facilitate penetration of the obturator through tissue, with the precise design of the taper not being critical. Suitable taper designs include faceted tapers, conical tapers, and the like. For shorter taper angles (i.e., sharper tips), less force is required to effect penetration. The present invention allows the use of sharper tips since the physician is warned as soon as the initial penetration is made. A handle or other structure will usually be provided at the proximal end of the shaft to facilitate manual pushing of the tapered distal end of the obturator through tissue. The dimensions of the shaft will be suitable for introduction into and use with conventional trocar cannulas, typically having a length in the range from about 5 cm to 30 cm, more typically from about 7.5 cm to 25 cm, and a diameter (for cylindrical shafts) in the range from 3 mm to 20 mm, usually from about 5 mm to 15 mm.

The features of the obturator described thus far are generally conventional and typical of obturators which are presently available for use in trocar systems used in laparoscopic surgery. The obturators of the present invention, however, will further comprise a mechanism for providing an audible signal substantially immediately upon entrance of the distal tip of the obturator entering an insufflated abdominal region of a patient undergoing laparoscopic or other least invasive surgical procedures. In particular, the audible signal will be produced in response to the superatmospheric pressure which exists as a result of insufflation, typically being a pressure in the range from about 10 mmHg to 15 mmHg.

The mechanism for producing the audible signal could take a variety of forms, including the use of an electrical pressure sensor or other signal transducer, or a mechanical pressure-responsive switch, in combination with an amplifier and speaker circuit. Generally, however, it will be desirable to employ a system with no moving parts which relies on producing an audible signal by relying on relatively low volume flow of the insufflation gas through the obturator once the tip of the obturator has penetrated into the superatmospheric region. Specifically, the preferred audible signal-producing mechanism of the present invention will comprise a "whistle" structure where superatmospheric insufflation gas enters an axial lumen of the obturator through one or more ports located very close to the distal tip of the tapered distal end of the obturator. Preferably, the port(s) will be located within 1 mm of the distal tip, more preferably within about 2 mm of the distal tip. In this way, the audible signal will be produced substantially immediately upon entry of the tip into the insufflated abdominal region, allowing the surgeon to take protective measures prior to any injury to the patient. A specific obturator design, in combination with an exemplary trocar cannula design, will now be described in connection with the drawings.

Referring to FIGS. 1 and 2, an exemplary trocar system 10 comprises an obturator 12 and a trocar cannula 14. The trocar cannula 14 includes a sleeve 16 having an open distal port 18. A flange 20 is located at the proximal end of the trocar cannula 14, and a trumpet valve assembly 22 is located between the proximal and distal ends, generally closer to the proximal end. The trumpet valve assembly 22 includes a sliding gate 24 having an actuator button 26 attached at one end thereof. A spring 28 is provided which holds the sliding gate 24 in a "normally closed" configuration. That is, a solid portion 30 of the gate 24 will normally close the trumpet valve assembly 22 when the button 26 is not depressed. In FIG. 2, however, the obturator 12 lies within an aperture 32 of the sliding gate 24, holding the valve assembly 22 open. It will be appreciated that obturator 12 may be passed into the trocar cannula 14 by first depressing button 26 on the trumpet valve assembly 22 to open the valve. After inserting the trocar 12, the valve will remain open so long as the obturator is in place. Such construction and operation of the trocar cannula 14 is conventional and known in the art.

The novel obturator 12 of the present invention will be described in more detail with reference to FIGS. 1, 3, and 3A. The obturator 12 includes an elongate shaft 40 having a tapered distal end 42 and a handle (palm rest) 44 at its proximal end. A plurality of pressure- or flow-sensing ports 46 are provided very near the distal tip 48 of the tapered tip 42. The ports 46 are connected to an axial lumen 50 via a smaller axial lumen 52, as best observed in FIG. 3. It will be appreciated that superatmospheric pressure present at the ports 46 will cause a flow of gas into the ports through the axial lumen 52 into the axial lumen 50.

A whistle structure is provided near the proximal end of the obturator 12. The whistle structure includes a flow-restrictive orifice 60 located adjacent a whistle aperture 62. The flow-restrictive orifice is located at the proximal end of the axial lumen 50 so that all gas entering through the ports 46 will eventually pass through the orifice 60. The flow-restrictive orifice 60 will increase pressure and thus cause the velocity of the gas to increase, and the rapid flow of the gases past and through the whistle aperture 62 will cause an audible sound (whistle). In this way, an audible signal will be provided to the surgeon whenever the distal ports 46 are exposed to superatmospheric insufflation pressures. The flow restrictive orifice is also beneficial since it limits the volume of insufflation gas which is lost during the time the whistle is sounded prior to removal of the obturator 12.

Figure 4:
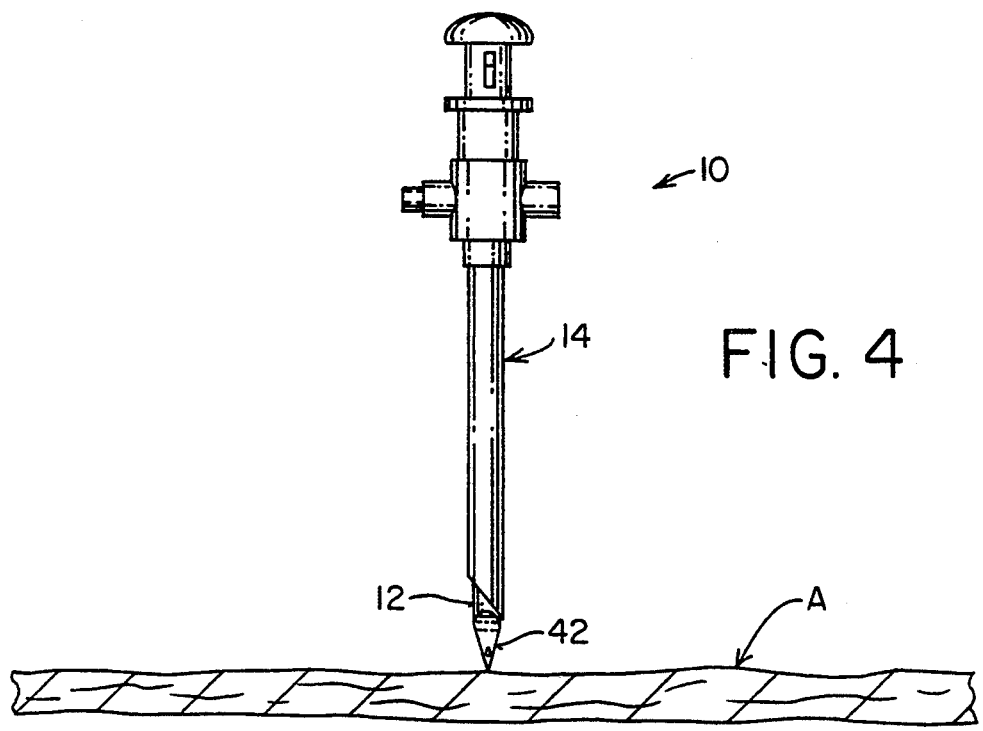
FIGS. 4–6 illustrate use of the trocar system of FIGS. 1 and 2 in introducing a trocar cannula through an abdominal wall according to the method of the present invention.
Figure 5:
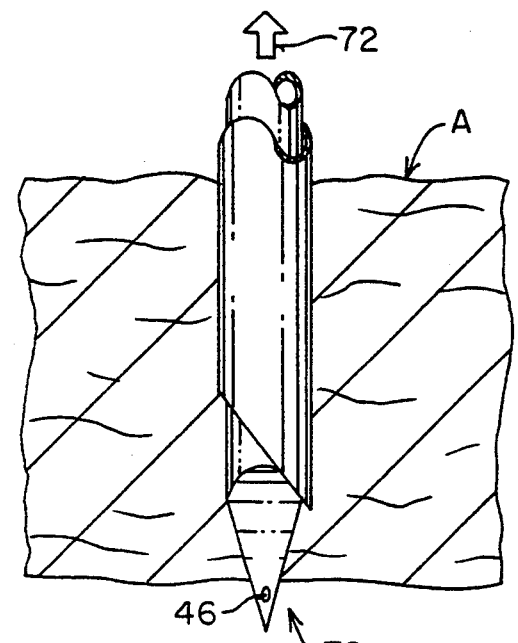

The method of the present invention will now be described in more detail with reference to FIGS. 4 and 5. The trocar system 10 of the present invention will be utilized with the obturator 12 initially in place within the trocar cannula 14 so that the tapered distal end 42 extends from the cannula. The physician will contact the tapered distal end 42 against a patient's abdomen A and apply pressure to the handle 44 to cause the tapered end to penetrate the tissue of the abdomen. At this point in the procedure, the trocar system will be oriented generally transversely to the abdominal wall. As soon as any one of the ports 46 pass through the abdominal wall and enter the insufflated region beneath the wall, the lumens 50 and 52 will be exposed to superatmospheric pressure, as illustrated in FIG. 5. Since the proximal end of the obturator remains exposed only to atmospheric pressure, a flow of gas will enter the port(s) 46, as indicated by arrow 70, and pass upward through the axial lumen 50, as indicated by arrow 72. A flow of gas will then enter the whistle structure, as described previously, providing for the desired audible signal.

Figure 6:
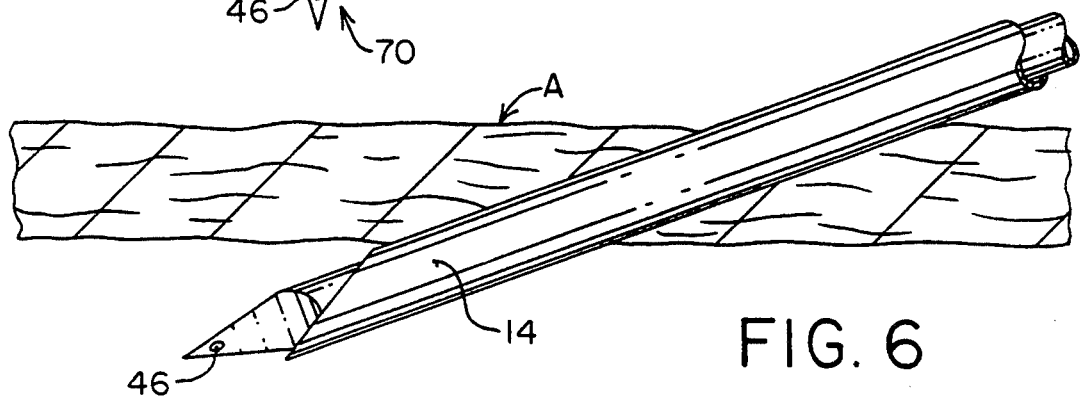

It is a particular advantage of the trocar system of the present invention that the physician will be warned almost immediately usually within 1 mm to 2 mm upon passage of the tip of the obturator 12 past the abdominal wall. As soon as the physician is aware of such passage, the trocar can be reoriented so that the obturator tip further penetrates into the abdominal cavity at a shallow angle, i.e., generally parallel to or axially aligned with the patient's body, as illustrated in FIG. 6. Previous trocar systems have not allowed such early precautions to be taken.

Although the foregoing invention has been described in some detail by way of illustration and example, for purposes of clarity of understanding, it will be obvious that certain changes and modifications may be practiced within the scope of the appended claims

What is claimed is:

1. An obturator for use with a trocar cannula, said obturator comprising:
   an elongate shaft having a proximal end and a tapered distal end; and
   means on the shaft for establishing a gas flow stream when gas pressure at the distal end of the shaft is greater than gas pressure at the proximal end of the shaft and producing an audible signal in response to said gas flow stream.

2. An obturator for use with a trocar cannula, said obturator comprising:
   an elongate shaft having a proximal end, a tapered distal end, and a lumen extending axially therethrough;
   at least one port open to the axial lumen located near the distal tip of the tapered distal end; and
   means at the proximal end of the shaft for producing an audible signal in response to superatmospheric pressure in the axial lumen.

3. An obturator as in claim 2, wherein the audible signal producing means comprises a flow-restrictive orifice and a whistle aperture formed in the elongate shaft, wherein the orifice and aperture are oriented so that superatmospheric conditions at the distal port will cause gas flow through the lumen, orifice, and aperture which in turn will cause a whistling sound.

4. An obturator as in claim 2, wherein the distal port is located within 2 mm of the distal tip of the tapered distal tip.

5. An obturator as in claim 2, wherein the elongate shaft has a length in the range form 7.5 cm to 25 cm and an outside diameter in the range from about 5 mm to 15 mm.

6. An obturator as in claim 2, further comprising a handle at the proximal end of the elongate shaft.

7. A trocar system comprising a trocar cannula and an obturator, wherein said obturator comprises
   an elongate shaft having a proximal end, a tapered distal end, and a lumen extending axially therethrough;
   at least one port open to the axial lumen located near the distal tip of the tapered distal end; and
   means at the proximal end of the shaft for producing an audible signal in response to superatmospheric pressure in the axial lumen.

8. A trocar system as in claim 7, wherein the audible signal producing means comprises a flow restrictive orifice and a whistle aperture formed in the elongate shaft, wherein the orifice and aperture are oriented so that superatmospheric conditions at the distal port will cause gas flow through the lumen, orifice, and aperture which in turn will cause a whistling sound.

9. A trocar system as in claim 7, wherein the distal port is located within 2 mm of the distal tip of the tapered distal tip.

10. A trocar system as in claim 7, wherein the elongate shaft has a length in the range form 7.5 cm to 25 cm and an outside diameter in the range from about 5 mm to 15 mm.

11. A trocar system as in claim 7, further comprising a handle at the proximal end of the elongate shaft.

12. A method for introducing a trocar cannula into an insufflated region of a patient's abdomen, said method comprising:
   advancing a combination trocar cannula and obturator through the abdominal wall, wherein the combination is oriented generally transversely to the abdominal wall and the obturator includes means for establishing a gas flow stream and producing an audible signal in response to said gas flow stream when its distal tip is exposed to superatmospheric pressure of the insulated region;

reorienting the combination trocar cannula and obturator into a more axial alignment with the abdominal wall after the audible signal is heard; and removing the obturator from the trocar cannula after the trocar cannula has reached a desired penetration depth.

13. A method for introducing a trocar cannula into an insufflated region of a patient's abdomen, said method comprising:

advancing a combination trocar cannula and obturator through the abdominal wall, wherein the combination is oriented generally transversely to the abdominal wall and the obturator includes an elongate shaft having a proximal end, a tapered distal end, a lumen extending axially therethrough, and a port located adjacent the tapered distal end, wherein entry of the port into the insufflated region causes a reflow of gas through the lumen which produces an audible signal;

reorienting the combination trocar cannula and obturator into a more axial alignment with the abdominal wall after the audible signal is heard; and removing the obturator from the trocar cannula after the trocar cannula has reached a desired penetration depth.

* * * * *